United States Patent
Bergstrom et al.

(10) Patent No.: US 7,002,045 B2
(45) Date of Patent: Feb. 21, 2006

(54) ORTHO ESTER-BASED SURFACTANT, ITS PREPARATION AND USE

(75) Inventors: Karin Bergstrom, Kungalv (SE); Per-Erik Hellberg, Svenshogen (SE)

(73) Assignee: Akso Nobel N.V., Arnhem (NL)

( * ) Notice: Subject to any disclaimer, the term of this patent is extended or adjusted under 35 U.S.C. 154(b) by 0 days.

(21) Appl. No.: 10/642,882

(22) Filed: Aug. 18, 2003

(65) Prior Publication Data

US 2004/0039235 A1 Feb. 26, 2004

Related U.S. Application Data

(63) Continuation of application No. 09/596,468, filed on Jun. 19, 2000, now abandoned, which is a continuation of application No. PCT/SE98/02239, filed on Dec. 8, 1998.

(51) Int. Cl.
C07C 41/60 (2006.01)
C11D 9/26 (2006.01)

(52) U.S. Cl. ........................ 568/595; 568/913; 568/918; 134/10; 210/708; 210/774; 510/109; 510/506; 8/404; 514/723

(58) Field of Classification Search ................ 568/595, 568/913, 918; 510/506, 535, 109; 516/72; 134/10; 210/708, 774; 8/404; 514/723
See application file for complete search history.

(56) References Cited

U.S. PATENT DOCUMENTS 3,903,006 A * 9/1975 Elliott et al. .................. 252/79

4,450,087 A * 5/1984 Askew et al. ................. 252/73

* cited by examiner

Primary Examiner—Rosalynd Keys
(74) Attorney, Agent, or Firm—Ralph J. Mancini

(57) ABSTRACT

The present invention relates to a new ortho ester-based surfactant, where the hydrophobic and hydrophilic parts are connected by ortho ester linkages to the molecule. The ortho ester has the formula

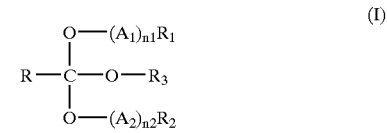

(I)

where R is hydrogen or an aliphatic group with 1–7 carbon atoms; $R_1$ is hydrogen or an alkyl group with 1–5 carbon atoms; $A_1$ is an alkyleneoxy group with 2–4 carbon atoms, the number of ethyleneoxy groups being at least 50% of the total number of alkyleneoxy groups; $n_1$ is a number between 1 and 30; $R_2$ is an aliphatic group with 5–22 carbon atoms; $A_2$ is an alkyleneoxy group with 3–4 carbon atoms; $n_2$ is a number between 0–30, provided that when $R_2$ is an aliphatic group with 5–6 carbon atoms $n_2$ is at least 1; $R_3$ is selected from the group consisting of $(A_1)_{n1}R_1$, $(A_2)_{n2}R_2$ and an alkyl group with 1–6 carbon atoms, where $A_1$, $n_1$, $R_1$, $A_2$, $n_2$ and $R_2$ have the same meaning as mentioned above; or a di- or polycondensate via any of the free hydroxy groups of the ortho ester. The ortho ester surfactants are stable in alkaline solutions, but are readily hydrolysed in acidic solutions to yield products that are not surface active. They are suitable to be used as emulsifiers or dispersants.

16 Claims, No Drawings

ORTHO ESTER-BASED SURFACTANT, ITS PREPARATION AND USE

The present application is a continuation U.S. application Ser. No. 09/596,468 filed Jun. 19, 2000, now abandoned, which is a continuation of International Application Number PCT/SE98/02239 filed on Dec. 8, 1998 which claims priority of Swedish Application Number 9704755-9 filed on Dec. 19, 1997.

FIELD OF THE INVENTION

The present invention relates to a new ortho ester-based surfactant, where the hydrophobic and hydrophilic parts are connected by ortho ester linkages to the molecule. The surfactants are stable in alkaline solutions, but are readily hydrolysed in acidic solutions to yield products that are not surface active.

BACKGROUND OF THE INVENTION

Surfactants are used in a variety of applications and processes, but once their task is fulfilled their presence is often undesirable. From an environmental point of view, it is a great advantage if products that ultimately end up in the environment are easily degradable, either biologically or by other means. Also, since surfactants have the ability to form emulsions and dispersions, which in most cases is the very reason for using them, they make the separation of hydrophobic material from the waste water obtained in industrial processes difficult.

In order to improve the degradability of surfactants and make the separation of hydrophobic material from waste water easier, it has been suggested in EP-A1-0 742 177 and EP-A1-0 742 178 to use hydrolysable aldehyde- and ketone-based surfactants. The surfactants, which contain acetal linkages, are stable in alkaline solutions but are hydrolysed in acidic solutions. Acetal-based surfactants are also described in EP-A3-0 054 366.

However, to effect complete hydrolysis the pH need to be lower and the reaction time longer for the acetals as compared to the ortho esters. This will result in a larger consumption of chemicals, and either give a water phase with an unacceptably low pH to be let out to the sewage treatment works or, if the waste water is neutralised, the formation of larger amounts of salt. Furthermore, there is only a small number of long-chain aldehydes that are commercially available, and consequently the range of acetal-based surfactants possible to obtain is limited. In addition the aldehydes are generally more difficult to produce than the corresponding alcohols, and are therefore more expensive.

Ortho ester surfactants have been described in EP-A1 564 402, where an ortho ester group is used for end-capping of nonionic surfactants. The products obtained are low-foaming, and can be used e.g. in machine dish-washing and bottle-cleaning. These products, however, will only marginally benefit from a better degradation, since a hydrolysis step will produce compounds that are still surface active.

SUMMARY OF THE INVENTION

The present invention generally relates to provide surfactants with at least as good emulsifying and dispersing ability as conventional types of surfactants, which in addition are readily cleavable and more easily biodegradable. More particularly, the invention contemplates ortho esters of the formula

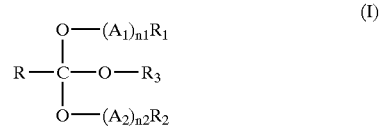

where R is hydrogen or an aliphatic group with 1–7 carbon atoms; $R_1$ is hydrogen or an alkyl group with 1–5 carbon atoms; $A_1$ is an alkyleneoxy group with 2–4 carbon atoms, the number of ethyleneoxy groups being at least 50% of the total number of alkyleneoxy groups; $n_1$ is a number between 1 and 30; $R_2$ is an aliphatic group with 5–22 carbon atoms; $A_2$ is an alkyleneoxy group with 3–4 carbon atoms; $n_2$ is a number between 0–30, provided that when $R_2$ is an aliphatic group with 5–6 carbon atoms $n_2$ is at least 1; $R_3$ is selected from the group consisting of $(A_1)_{n1}R_1$, $(A_2)_{n2}R_2$ and an alkyl group with 1–6 carbon atoms, where $A_1$, $n_1$, $R_1$, $A_2$, $n_2$ and $R_2$ have the same meaning as mentioned above; or a di- or polycondensate via any of the free hydroxy groups of the ortho ester.

DETAILED DESCRIPTION OF THE INVENTION

The aim of the present invention is to provide surfactants with at least as good emulsifying and dispersing ability as conventional types of surfactants, which in addition are readily cleavable and more easily biodegradable. Their degradation products should also be environmentally friendly, and not exhibit any essential surface activity. Further, this new kind of surfactants should be easy to produce. Surprisingly, it has now been found that surfactants based on an ortho ester according to formula

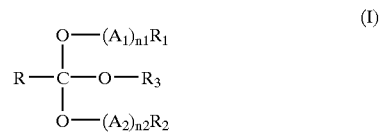

where R is hydrogen or an aliphatic group with 1–7 carbon atoms; $R_1$ is hydrogen or an alkyl group with 1–5 carbon atoms, preferably $R_1$ is an alkyl group with 1–4 carbon atoms; $A_1$ is an alkyleneoxy group with 2–4 carbon atoms, the number of ethyleneoxy groups being at least 50% of the total number of alkyleneoxy groups; $n_1$ is a number between 1 and 30, preferably between 2–25; $R_2$ is an aliphatic group with 5–22 carbon atoms, preferably 8–22; $A_2$ is an alkyleneoxy group with 3–4 carbon atoms; $n_2$ is a number between 0–30, preferably between 0–20, provided that when $R_2$ is an aliphatic group with 5–6 carbon atoms $n_2$ is at least 1, preferably at least 2; $R_3$ is selected from the group consisting of $(A_1)_{n1}R_1$, $(A_2)_{n2}R_2$ and an alkyl group with 1–6 carbon atoms, preferably 1–4, where $A_1$, $n_1$, $R_1$, $A_2$, $n_2$ and $R_2$ have the same meaning as mentioned above; or a di- or polycondensate via any of the free hydroxy groups of the ortho ester; display the above-mentioned properties. To strengthen the hydrophilic part of the molecule the groups $A_1$ may consist only of ethyleneoxy groups.

The surfactants of formula I have a good emulsifying and dispersing ability, and are preferably used in applications where the rapid cleavability offers an advantage, e.g. for hard surface cleaning, deinking, viscose processing, disinfection and in fibre and textile processes such as dyeing and scouring. They are also low-foaming, which is an advantage in many applications. When used for cleaning of hard surfaces they exhibit comparable or better effects than traditional surface active nonionic alkylene oxide adducts. The emulsifying ability of this surfactant type is further demonstrated by the formulation of an emulsion for a pesticide. This formulation is of comparable stability to a formulation obtained with an optimized nonionic emulsifier of the traditional type.

The cleavage of the ortho ester-based surfactant is promoted to a high degree by decreasing the pH and increasing the temperature. The ortho ester could also be used as an emulsifier/dispersant at a lower pH, e.g. at a pH of 5, if the process is fast enough, and consequently be cleaved at the same pH. When compared to the cleavage of an acetal-based surfactant at the same conditions, the ortho ester-based surfactant is cleaved much more rapidly. The cleavage results in degradation products that lack the ability to behave as surfactants, e.g. to form emulsions, which is demonstrated in Example 12. The rapid cleavability of the ortho esters of the present invention presents a special advantage in application areas where the separation of an oil phase from the water phase is desirable, e.g. for waste water treatment, in the working-up of emulsions formed when cleaning hard surfaces, in deinking and textile processes, such as scouring.

The invention also relates to a process for making the ortho ester-based surfactants, where low molecular weight ortho esters are used as starting materials. These low molecular weight ortho esters are reacted with a hydrophobic component, which is an alcohol, and preferably an end-capped hydrophilic component, which is preferably a polyethylene oxide adduct. The molar amounts of the reactants are preferably 1–2 moles of the hydrophilic component per mole orthoester and 1–2 moles of the hydrophobic component per mole ortho ester.

By this process surface active ortho esters are obtained, where the hydrophobic and hydrophilic parts each individually is connected by ortho ester bonds to the molecule.

The ortho ester-based surfactants of the present invention can be produced by reacting an ortho ester of the general formula

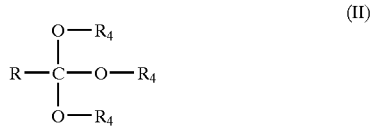

(II)

where R has the same meaning as in Formula I and $R_4$ is an alkyl group with 1–6 carbon atoms, preferably 1–4, in one or several steps, with reactants having the formulas $HO(A_1)_{n1}R_1$ and $HO(A_2)_{n2}R_2$, where $R_1, R_2, A_1, A_2, n_1$ and $n_2$ have the same meaning as in Formula I, while evaporating alcohols with the formula $R_4OH$, where $R_4$ has the same meaning as above. The reaction preferably is performed in the presence of an acid, e.g. methanesulphonic acid, p-toluenesulphonic acid or citric acid. The temperature is increased during the reaction and is finally reaching 140 to 220° C. The alcohols $R_4OH$, that are liberated during the reaction, are gradually evaporated from the reaction mixture. In the final phase of the reaction vacuum is applied to remove the residual amounts of alcohols, thereby driving the reaction to completion.

Suitable examples of ortho esters II are methyl or ethyl ortho formate, methyl or ethyl ortho acetate and other low molecular weight ortho esters that are commercially available.

The hydrophobic part of the molecule may be derived from an alcohol $R_2OH$, or an alkoxylate thereof. The alcohol could either be synthetic or natural. Suitable examples of alkyl groups $R_2$ are 2-ethylhexyl, octyl, decyl, coco alkyl, lauryl, oleyl, rape seed alkyl and tallow alkyl. Other suitable hydrocarbon groups $R_2$ are those obtained from oxoalcohols, Guerbet alcohols, and methyl substituted alcohols with 2–4 groups having the formula —CH(CH$_3$)— included in the alkyl chain. The alcohols may also be propoxylated or butoxylated.

The hydrophilic part of the molecule is preferably derived from polyethylene glycols, that are end-capped, preferably with a methyl or ethyl group, and have a molecular weight between 100 and 2000. The choice of hydrophobic and hydrophilic parts and the relative amounts of them will of course vary between different applications, to satisfy their demands for a specific HLB, cloud point etc.

In another embodiment the present invention relates to the use of an ortho ester according to formula I in a process comprising
a) emulsifying or dispersing a hydrophobic component in water at a pH of 6 or above, preferably at pH 7 or above, in the presence of an ortho ester according to the present invention,
b) lowering the pH or increasing the temperature of the emulsion or dispersion, or a combination thereof, and thereby breaking the emulsion or dispersion, and
c) separating the hydrophobic component from water.

The surfactant is normally used as an emulsifier or dispersant at a pH of 9 or above, but could also be used down to a pH of ca 6. The waste water obtained as a result of the performance of the surfactant in step a is then treated in accordance with b. The pH of the emulsion or dispersion is preferably reduced to a pH of between 4 and 6. If needed, the temperature may be raised, preferably to between 20 and 60° C. to further promote the cleavage. In some circumstances, when the pH during the emulsification is low enough, it might suffice to raise the temperature. The lower the pH and the higher the temperature, the faster the cleavage will occur. In most circumstances it might be more convenient to lower the pH further than to raise the temperature above ambient, since the latter will often require a large energy input.

The above-mentioned process could be used in a variety of applications. One major application is the cleaning of hard surfaces, for example in connection with vehicle cleaning and the cleaning of storage tanks and tankers, where the ortho ester surfactant is used at alkaline pH as an emulsifier or dispersant for the hydrophobic dirt or fluid. When the surface has been cleaned, the waste water is acidified whereby the surfactant is cleaved. This causes the emulsion or dispersion to break, and the hydrophobic material is separated from the water phase.

In an analogous manner, the hydrophobic ink obtained in a deinking process, the surplus of hydrophobic dye from a textile dyeing process and the dirt from a textile scouring process could be emulsified or dispersed by the surfactants, and later on removed from the process waste water.

The ortho ester surfactants also benefit from a better biodegradability than the corresponding conventional non-ionic surfactants. When subjected to a neutral or slightly acidic pH in a sewage-treatment plant, the ortho ester surfactants are cleaved to yield non-toxic substances that are essentially not surface active. These substances would be more easily biodegraded than an intact surface active molecule would be. A comparison between a traditional nonionic surfactant and an ortho ester surfactant according to the present invention (see Example 14) shows the latter to be more easily biodegradable.

The present invention is further illustrated by the following Examples.

EXAMPLE 1

1.5 moles of a $C_9$–$C_{11}$ linear primary alcohol (Dobanol 91 from Shell), 1.5 moles of diethylene glycol monoethyl ether ethoxylate (diethylene glycol monoethyl ether+2 moles of ethylene oxide), 1 mole of triethyl orthoformate and 0.2% w/w of methanesulphonic acid were mixed together at ambient temperature. The temperature of the reaction mixture was gradually raised, and finally, after ca 4 hours, a temperature of 150–200° C. was reached. Ethanol, that was liberated during the reaction, was continuously distilled off. In the final phase of the reaction, vacuum was applied to facilitate the removal of ethanol. A total of 30.8 g of ethanol was collected, which corresponds to 92% of the theoretical amount. The distillate was analysed by $^1$H-NMR and the product was analysed by $^1$H-NMR and $^{13}$C-NMR. According to the analyses there was no unreacted triethyl orthoformate left.

EXAMPLE 2

1.05 moles of 2-ethylhexanol propoxylate (2ethylhexanol+13 moles of propylene oxide), 1.05 moles of diethylene glycol monomethyl ether ethoxylate (diethylene glycol monomethyl ether+18 moles of ethylene oxide), 1.0 mole of triethyl orthoformate and 1% w/w of anhydrous citric acid were mixed and a reaction was performed under the same conditions as in Example 1. A total of 10.2 g of ethanol was distilled off, which corresponds to 92% of the theoretical amount. The same analyses as in Example 1 were performed. No unreacted triethyl orthoformate was found.

EXAMPLE 3

1.5 moles of 2-ethylhexanol, 1.5 moles of a monomethyl-blocked polyethylene glycol having a mean molecular weight of 550, 1 mole of triethyl orthoformate and 0.2% w/w of methanesulphonic acid were mixed. The same procedure as in Example 1 was followed. A total of 18.2 g of ethanol was collected, which corresponds to 98% of the theoretical amount. The same analyses as in Example 1 were performed. No unreacted triethyl orthoformate was found. According to the NMR analysis more than 70% of the product consists of three surface active components specified below. The number of ethoxy groups that has not been substituted is denoted by x, the number of 2-ethylhexyl groups by y and the number of end-capped polyoxyethylene groups by z.

| Component nr | x | y | z |
|---|---|---|---|
| 1 | 1 | 1 | 1 |
| 2 | 0 | 2 | 1 |
| 3 | 0 | 1 | 2 |

EXAMPLE 4

The procedure is the same as in Example 1, except that 2-ethylhexanol+2.4 moles of propylene oxide and monomethyl-blocked polethylene glycol having a mean molecular weight of 550 are used as the hydrophobic and hydrophilic components respectively. The same analyses as in Example 1 were performed. No unreacted triethyl orthoformate was found.

EXAMPLE 5

The procedure is the same as in Example 1, except that n-octanol and monomethyl-blocked polyethylene glycol having a mean molecular weight of 350 are used as the hydrophobic and hydrophilic components respectively. The same analyses as in Example 1 were performed. No unreacted triethyl orthoformate was found.

EXAMPLE 6

0.152 moles of hexadecanol, 0.152 moles of monomethyl-blocked polethylene glycol having a mean molecular weight of 750, 0.101 moles of triethyl orthoformate and 0.15% w/w of anhydrous citric acid were mixed together. The temperature of the reaction mixture was gradually raised from 22° C. to 155° C. during the course of 30 min. Ethanol, that was liberated during the reaction, was continuously distilled off. When the temperature had reached 155° C., the pressure was slowly reduced to 3 mbar and held there for 20 min to facilitate the removal of ethanol. A total of 13.7 g of ethanol was collected, which corresponds to 99% of the theoretical amount. The distillate was analysed by $^1$H-NMR and the product was analysed by $^1$H-NMR and $^{13}$C-NMR. According to the analyses there was no unreacted triethyl orthoformate left, and 60% of the product mixture consists of three surface active components corresponding to the ones specified in the table of Example 3.

EXAMPLE 7

The procedure is the same as in Example 6, except that 2-ethylhexanol+2 moles of propylene oxide and monomethyl-blocked polethylene glycol having a mean molecular weight of 550 are used as the hydrophobic and hydrophilic components respectively. The same analyses as in Example 6 were performed. No unreacted triethyl orthoformate was found.

EXAMPLE 8

The procedure is the same as in Example 6, except that a $C_9$–$C_{11}$ linear primary alcohol (Dobanol 91 from Shell) and monomethyl-blocked polethylene glycol having a mean molecular weight of 470 are used as the hydrophobic and hydrophilic components respectively. The same analyses as in Example 6 were performed. No unreacted triethyl orthoformate was found.

EXAMPLE 9

The biodegradability of the ortho ester-based surfactant described in Example 1 was investigated by the ?closed bottle test? as described in OECD Test 301D. The surfactant reached 82% biodegradation after 28 days, and is consequently classified as easily biodegradable.

EXAMPLE 10

To evaluate the cleaning efficiency of formulations containing an ortho ester-based surfactant of the present invention, the following cleaning test was used: Alumina plates (41×15 mm) coated with C14 marked triolein (glycerol trioleate from Amersham) were put in a holder and washed in a Terg-O-Tometer by turning the holders back and forth through the surfactant solution with a velocity of 50 rpm during a period of 5 min. The test was performed at 20 and 40° C., using the formulations I, II and III in the Table below, where I is a reference formulation containing a traditional nonionic surfactant. The formulations were diluted with tap water 1:100 prior to use. After the cleaning step the holders were dipped for 5 seconds in tap water holding a temperature of 20° C.

| Component | Formulation I % by weight of component | Formulation II % by weight of component | Formulation III % by weight of component |
|---|---|---|---|
| $C_9$–$C_{11}$ alcohol + 4EO | 5 | — | — |
| Ortho ester mixture of Ex. 4 | — | 5 | — |
| Ortho ester mixture of Ex. 7 | — | — | 5 |
| Octyliminodipropionate | 2.8 | 2.8 | 2.8 |
| Tetrapotassium pyrophosphate | 6 | 6 | 6 |
| Metasilicate | 4 | 4 | 4 |
| Water | balance | Balance | balance |

The plates were transferred to vials containing scintillation liquid (Ultima Gold from Packard) with the ability to dissolve fat, and were shaken at 300 rpm for 20 minutes. The plates were removed from the vials, and the liquid was analysed for radioactivity in a scintillation analyser (TriCarb 1900CA from Packard). The result is reported as % washed-away fat as compared to coated plates that have not been washed according to the procedure above.

| Formulation | % washed-away fat at 20° C. | % washed-away fat at 40° C. |
|---|---|---|
| I | 57.9 | 85.0 |
| II | 87.6 | 79.6 |
| III | 84.2 | 91.2 |

This example shows that the ortho ester surfactants are as good cleaners for hard surfaces as the nonionic surfactant used as a reference.

EXAMPLE 11

The wetting ability of ortho ester-based surfactants according to the present invention was estimated by contact angle measurements.

The test solutions were the formulations I (reference), II and III that were used in Example 10. The formulations were used undiluted. The contact angle was measured against a hydrophobic polymeric material (Parafilm PM-992 from American Can Company) with a Ramé-Hart NRL C.A. Goniometer. The measurements were made after 1 min, and each value is the average of 10 measurements. The results are summarised in the Table below.

| Formulation | Contact angle after 1 min (°) |
|---|---|
| I | 35.8 |
| II | 35.3 |
| III | 34.4 |

The results show that the wetting ability of the ortho ester-based surfactants according to this invention is comparable to the wetting ability of the reference compound.

EXAMPLE 12

A comparison is made between the ortho ester-based surfactant produced according to Example 1, an ortho ester end-blocked surfactant and an acetal-based surfactant, regarding their emulsifying ability at different pH-values.

The oil phase used in all experiments is n-decane, and the water phase consists of different buffer solutions. Sudan Red B is added as a colorant for the emulsion. The surfactants used are:

A) Ortho ester-based surfactant according to Example 1
B) A $C_{10}$-$C_{11}$ linear primary alcohol+8 moles of ethylene oxide that is end-blocked with triethyl orthoformate (synthesized according to the procedure described in EP-A1-0 564 402)
C) The acetal between n-decanal and glycerol ethoxylated with 4 moles of ethylene oxide (synthesized according to the procedure described in EP-A1-0 742 177)

Procedure:

7.5 ml n-decane, 7.5 ml buffer solution, 0.3 g surfactant and 2 drops of Sudan red B are placed in a sealable test tube, which is manually shaken for one minute before the first measurement. The emulsion is allowed to separate, and after 3 minutes the degree of separation is measured as a/b×100, where a is mm clear lower phase, and b is mm clear water phase before emulsifying.

Between the measurements the test tubes are continuously shaken at 1000 rpm in the horizontal position by an IKA-VIBRAX-VXR apparatus. Before each new measurement the test tube is manually shaken for 30 s to completely reemulsify the mixture.

The test is performed at 22 and 50° C. For the test at 50° C. n-decane and buffer solution is preheated before the surfactant is added.

| pH | Time for 100% Separation of Emulsions with A At 22° C. | Time for 100% separation of emulsions with A at 50° C. | Time for 100% separation of emulsions with C at 22° C. |
|---|---|---|---|
| 2 | <5 minutes | <1 minute | >35 days |
| 3 | <5 minutes | <1 minute | — |
| 4 | <39 minutes | <10 minutes | — |
| 5 | <120 minutes | <15 minutes | — |
| 6 | ca 55 hours | <3 hours | — |
| 7 | >8 days | <22 hours | — |
| 8 | >15 days | ca 29 hours | — |
| 9 | — | >16 days | — |
| 10 | >40 days | >40 days | — |
| 11.5 | >40 days | >40 days | — |

— test not performed

At 22° C. surfactant A is readily hydrolysed at pH-values below 5, which results in a loss of surface activity causing the emulsions to separate. At 50° C. the hydrolysis is rapid in this pH range, yielding separation times below 15 minutes. As expected, the hydrolysis is slow at alkaline pH.

To obtain an acceptable hydrolysis time for C, 20% $H_2SO_4$ was added. This resulted in more than 3 hours time for 100% separation, whereas for an addition of 5% $H_2SO_4$, more than 72 hours was needed.

The emulsion produced with surfactant B is only marginally effected by pH. Still after 11 days at a pH of 2 and 22° C., only a separation of 11% is obtained. This is expected since the surface activity of B does not disappear when the ortho ester bond is broken.

These above results show the superiority of surfactant A to surfactant B and C regarding ease of hydrolysis at acid pH-values.

EXAMPLE 13

To further investigate the emulsion separation obtained at a pH of 5, two other kinds of oils were emulsified by the same surfactants A and C that were used in Example 8. For a comparison with a conventional nonionic surfactant, a $C_9$–$C_{11}$ alcohol+4 moles of ethylene oxide was used (surfactant D). The oils used were refined soy bean oil (produced by Karlshamn) and diesel oil, and the water phase consists of a pH 5 buffer solution.

Procedure:

At room temperature 200 ml oil, 300 ml buffer solution and 6 g surfactant are placed in a 500 ml reactor equipped with a mechanical stirrer of the propeller type. The reactor has an outlet at the bottom. The mixture is vigorously stirred at ca 500 rpm for 90 minutes. The emulsion that is formed is allowed to stand for 5 minutes, after which 250 ml liquid is drained off through the bottom outlet during ca 1 minute. The sample is left for 3 hours, after which the volume of oil and/or emulsion is measured. The result is presented as % v/v referring to the total volume of the sample. The values obtained are collected in the table below.

| Surfactant | pH | oil | % oil/emulsion in sample |
| --- | --- | --- | --- |
| A | 5 | soy bean | 4.0 |
| C | 5 | soy bean | 35.5 |
| D | 5 | soy bean | 51.6 |
| A | 5 | diesel | 0.8 |
| C | 5 | diesel | 75.9 |
| D | 5 | diesel | 72.8 |

The amount of oil and/or emulsion in a sample reflects the rate of hydrolysis of the surfactants. The results obtained show clearly that the use of the cleavable ortho ester-based surfactant A facilitates the separation of the oil phase from emulsions containing vegetable oil as well as petroleum based oil. The rate of emulsion separation at pH 5 is substantially higher using this ortho ester-based surfactant as compared to using the acetal-based surfactant C. When using the conventional nonionic surfactant D the rate of separation is still slower.

EXAMPLE 14

A formulation for a pesticide containing an ortho ester-based surfactant is compared to a standard formulation containing a traditional nonionic surfactant.

| Component | Formulation I amount of component (g/l) | Formulation II amount of component (g/l) |
| --- | --- | --- |
| Dimethoate | 200 | 200 |
| Ortho ester mixture of Example 2 | 50 | — |
| $C_8$-alcohol alkoxylate (EO/PO), MW 1800 | — | 50 |
| Cyclohexanone | 301 | 301 |
| Xylene | 413 | 413 |

5 ml of each formulation was emulsified in 95 ml of water, and the emulsions were transferred to 100 ml test tubes. The separation of the emulsions were noted as % v/v of clear upper phase at certain time intervals. The results are summarized in the table below.

| Formulation | Time | Separation (% v/v) |
| --- | --- | --- |
| I | 30 minutes | 0 |
| I | 1 hour | 0.5 |
| I | 2 hours | 0.5 |
| II | 30 minutes | 0 |
| II | 1 hour | 0 |
| II | 2 hours | 0 |

The formulation containing the ortho ester-based surfactant yielded an emulsion that was of comparable stability to the emulsion obtained by formulation II, which contains a traditional nonionic surfactant. However, the ortho ester-based surfactant has the advantage to be more easily cleaved to non-surface active compounds, and has therefore a better environmental profile than the conventional nonionic surfactant. The biodegradability of the ortho ester-based surfactant according to the ?closed bottle test? was 37% after 28 days and 41% after 42 days, whereas for the corresponding conventional surfactant 18% was degraded after 28 days and 35% after 112 days.

We claim:

1. An ortho ester surfactant of the formula

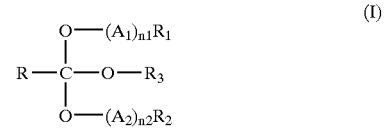

(I)

where R is hydrogen or an aliphatic group with 1–7 carbon atoms; $R_1$ is hydrogen or an alkyl group with 1–5 carbon atoms; $A_1$ is an alkyleneoxy group with 2–4 carbon atoms, the number of ethyleneoxy groups being at least 50% of the total number of alkyleneoxy groups; $n_1$ is a number between 1 and 30; $R_2$ is an aliphatic group with 5–22 carbon atoms; $A_2$ is an alkyleneoxy group with 3–4 carbon atoms; $n_2$ is a number between 0–30, provided that when $R_2$ is an aliphatic group with 5–6 carbon atoms $n_2$ is at least 1; $R_3$ is selected from the group consisting of $(A_1)_{n1}R_1$, $(A_2)_{n2}R_2$ and an alkyl group with 1–6 carbon atoms, where $A_1$, $n_1$, $R_1$, $A_2$, $n_2$ and $R_2$ have the same meaning as mentioned above; or a di- or polycondensate via any of the free hydroxy groups of the ortho ester.

2. The ortho ester surfactant of claim 1, wherein $R_1$ is an alkyl group with 1–4 carbon atoms.

3. The ortho ester surfactant of claim 1 wherein $n_1$ is a number between 2–25 and $n_2$ is a number between 0–20.

4. The ortho ester surfactant of claim 1 wherein $n_2$ is 0, $R_2$ is an aliphatic group with 8–22 carbon atoms and $A_1$ is an ethyleneoxy group.

5. A process for the preparation of the ortho ester surfactant of claim 1 which comprisesz reacting an ortho ester of the general formula

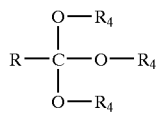

where R is hydrogen or an aliphatic group with 1–7 carbon atoms and $R_4$ is an alkyl group with 1–6 carbon atoms, in one or several steps, with reactants having the formulas $HO(A_1)_{n1}R_1$ and $HO(A_2)_{n2}R_2$, wherein $R_1$ is hydrogen or an alkyl group with 1–5 carbon atoms; $R_2$ is an aliphatic group with 5–22 carbon atoms; $A_2$ is an alkyleneoxy group with 3–4 carbon atoms; $A_1$ is an alkyleneoxy group with 2–4 carbon atoms, the number of ethyleneoxy groups being at least 50% of the total number of alkyleneoxy groups; $n_1$ is a number between 1 and 30; and $n_2$ is a number between 0–30, provided that when $R_2$ is an aliphatic group with 5–6 carbon atoms $n_2$ is at least 1, while evaporating alcohols with the formula $R_4OH$, where $R_4$ has the same meaning as above.

6. An emulsifying agent which comprises at least one ortho ester of claim 1.

7. A dispersing agent that comprises at least one ortho ester of claim 1.

8. A cleaning or scouring composition that comprises the ortho ester of claim 1.

9. A method of separating a hydrophobic component from an aqueous system that comprises
   a) emulsifying or dispersing said hydrophobic component in said aqueous system at a pH of 6 or above in the presence of an ortho ester in accordance with claim 1,
   b) lowering the pH or increasing the temperature of the emulsion or dispersion resulting from step a), or a combination thereof, and thereby breaking the emulsion or dispersion, and
   c) separating the hydrophobic component from the aqueous system.

10. The method of claim 9 wherein the temperature in step b is raised to between 20 and 60° C.

11. The method of claim 9 wherein the pH in step b is between 4 and 6.

12. The method of claim 9, wherein said hydrophobic component is hydrophobic ink.

13. A pesticidal formulation that comprises at least one ortho ester of claim 1.

14. An alkaline hard surface cleaner that comprises at least one ortho ester surfactant according to claim 1.

15. A method for cleanIng a hard surface contaminated with hydrophobic dirt which comprises applying to said surface an aqueous, alkaline hard surface cleaner according to claim 14 in an amount effective for said surfactant in said cleaner to disperse the dirt from said hard surface thereby forming an aqueous wastewater stream, followed by acidifying said wastewater stream thereby causing the hydrophobic dirt to separate from the aqueous phase.

16. An orthoester surfactant of the formula

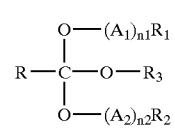

where R is hydrogen or an aliphatic group with 1–7 carbon atoms; $R_1$ is hydrogen or an alkyl group with 1–5 carbon atoms; $A_1$ is an alkyleneoxy group with 2–4 carbon atoms, the number of ethyleneoxy groups being at least 50% of the total number of alkyleneoxy groups; $n_1$ is a number between 1 and 30; $R_2$ is an aliphatic group with 5–22 carbon atoms; $A_2$ is an alkyleneoxy group with 3–4 carbon atoms; $n_2$ is a number between 0–30, provided that when $R_2$ is an aliphatic group with 5–6 carbon atoms $n_2$ is at least 1; $R_3$ is selected from the group consisting of $(A_1)_{n1}R_1$, $(A_2)_{n2}R_2$ and an alkyl group with 1–6 carbon atoms, where $A_1$, $n_1$, $R_1$, $A_2$, $n_2$ and $R_2$ have the same meaning as mentioned above; or a di- or polycondensate via any of the free hydroxy groups of the ortho ester, wherein said orther ester surfactant is prepared in accordance with the process of claim 5.

* * * * *

UNITED STATES PATENT AND TRADEMARK OFFICE
CERTIFICATE OF CORRECTION

| | | |
|---|---|---|
| PATENT NO. | : 7,002,045 B2 | Page 1 of 1 |
| APPLICATION NO. | : 10/642882 | |
| DATED | : February 21, 2006 | |
| INVENTOR(S) | : Karin Bergstrom and Per-Erik Hellberg | |

It is certified that error appears in the above-identified patent and that said Letters Patent is hereby corrected as shown below:

Title Page, Assignee Information,  change "Akso Nobel N.V., Arnhem (NL)"
to --Akzo Nobel N.V., Arnhem (NL)--

Col. 11, Line 7,  change "comprisesz"
to --comprises--

Col. 12, Line 12,  change "cleanIng"
to --cleaning--

Signed and Sealed this

Sixth Day of May, 2008

JON W. DUDAS
*Director of the United States Patent and Trademark Office*